United States Patent
Hofman (10) Patent No.: US 8,640,556 B2
(45) Date of Patent: Feb. 4, 2014

(54) AUTOMATED ASEPTIC SAMPLING WORKSTATION AND SAMPLE COLLECTION DEVICES THEREFORE

(75) Inventor: Jan Hofman, Vlaardingen (NL)

(73) Assignee: Alfa Wassermann, West Caldwell, NJ (US)

( * ) Notice: Subject to any disclaimer, the term of this patent is extended or adjusted under 35 U.S.C. 154(b) by 443 days.

(21) Appl. No.: 12/959,647

(22) Filed: Dec. 3, 2010

(65) Prior Publication Data

US 2012/0137793 A1 Jun. 7, 2012

(51) Int. Cl.
| | | |
|---|---|---|
| *G01N 1/14* | (2006.01) | |
| *G01N 1/34* | (2006.01) | |
| *F16K 11/22* | (2006.01) | |
| *G01N 1/20* | (2006.01) | |

(52) U.S. Cl.
CPC *G01N 1/14* (2013.01); *F16K 11/22* (2013.01); *G01N 1/2035* (2013.01); *G01N 2001/205* (2013.01)
USPC .................. 73/864.34; 73/863.01; 73/863.02; 73/863.31; 73/863.83; 73/863.86

(58) Field of Classification Search
CPC ....... C12M 33/06; C12M 37/00; F16K 11/22; F16K 27/00
USPC ............... 73/863.01–863.03, 863.31, 863.83, 73/863.85–863.86, 864.34
See application file for complete search history.

(56) References Cited

U.S. PATENT DOCUMENTS

| 2,736,201 | A | * | 2/1956 | Ohlsen et al. .......... 73/863.86 X |
| 3,071,961 | A | * | 1/1963 | Heigl et al. .................. 73/54.08 |
| 3,095,889 | A | * | 7/1963 | Barroll et al. .................... 137/14 |
| 3,116,210 | A | * | 12/1963 | Roguin et al. ................. 376/253 |

(Continued)

FOREIGN PATENT DOCUMENTS

| EP | 0086098 | 8/1983 |
| EP | 0637712 | 2/1995 |

(Continued)

OTHER PUBLICATIONS

Extended European Search Report dated Jul. 12, 2012 for European patent application No. 11009544.5.

(Continued)

*Primary Examiner* — Thomas P Noland
(74) *Attorney, Agent, or Firm* — Ohlandt, Greeley, Ruggiero & Perle, LLP (57) ABSTRACT

An automated sample collection workstation is provided. The workstation includes a processor, a peristaltic pump, a valve actuator, and an algorithm. The peristaltic pump and the valve actuator are in electrical communication with the processor. The valve actuator can move a plurality of valves, when disposed therein, among an off position, a flush position, and a sample position. The algorithm is resident on the processor and is configured to: move all of the valves to the off position and place the pump in an off state when no sampling or flushing is required, move all of the valves to the flush position and place the pump in an on state for a predetermined flush time period when flushing is required, and move a respective one of the valves to the sample position, move any of the valves upstream of the respective valve to the flush position, and place the pump to the on state for a predetermined sample time period when a sample is required.

16 Claims, 8 Drawing Sheets

(56) References Cited

U.S. PATENT DOCUMENTS

| | | | |
|---|---|---|---|
| 3,411,342 A * | 11/1968 | Liermann | 73/61.41 |
| 3,848,581 A | 11/1974 | Cinqualbre et al. | |
| 4,454,772 A | 6/1984 | Brunner et al. | |
| 4,628,749 A * | 12/1986 | Rafter, Jr. | G01N 1/2035 |
| 5,433,120 A * | 7/1995 | Boyd et al. | G01N 1/2035 |
| 5,460,204 A * | 10/1995 | Rossi | 137/884 |
| 5,654,201 A * | 8/1997 | Capuano | 436/129 |
| 5,711,916 A | 1/1998 | Riggs et al. | 422/83 |
| 6,032,543 A | 3/2000 | Arthun et al. | 73/863.84 |
| 7,074,364 B2 * | 7/2006 | Jahn et al. | 422/62 |
| 7,377,686 B2 | 5/2008 | Hubbard | |
| 7,381,375 B2 | 6/2008 | Ravkin et al. | |
| 7,467,890 B2 | 12/2008 | Patzek, IV | 366/165.1 |
| 7,560,071 B2 | 7/2009 | Nichols et al. | 422/63 |
| 7,578,205 B2 | 8/2009 | Belongia | |
| 7,588,728 B2 | 9/2009 | Clark et al. | |
| 7,891,860 B2 | 2/2011 | Hubbard | |
| 7,921,740 B2 | 4/2011 | Furey et al. | |
| 8,007,743 B2 | 8/2011 | Clark et al. | |
| 2001/0010318 A1 | 8/2001 | Saveliev et al. | 222/148 |
| 2001/0048899 A1 | 12/2001 | Marouiss et al. | 422/100 |
| 2003/0116487 A1 | 6/2003 | Petersen | |
| 2006/0279737 A1 * | 12/2006 | Chinowsky et al. | 356/445 |
| 2007/0128087 A1 | 6/2007 | Cannizzaro et al. | 422/119 |
| 2008/0130405 A1 | 6/2008 | Hubbard | |
| 2009/0143546 A1 * | 6/2009 | Fouarge et al. | 526/64 |
| 2010/0066374 A1 * | 3/2010 | Trygstad et al. | 324/321 |
| 2010/0154569 A1 | 6/2010 | Guedon | |
| 2010/0269918 A1 | 10/2010 | Rudolph | |
| 2011/0024375 A1 | 2/2011 | Reinbigler et al. | |
| 2011/0201100 A1 | 8/2011 | Proulx et al. | |
| 2012/0000566 A1 | 1/2012 | Morrissey et al. | |
| 2012/0061332 A1 | 3/2012 | Kas et al. | |
| 2012/0223517 A1 | 9/2012 | Morrissey et al. | |
| 2012/0315189 A1 | 12/2012 | Scott | |

FOREIGN PATENT DOCUMENTS

| | | | | |
|---|---|---|---|---|
| FR | 2358601 | | 2/1978 | |
| GB | 1506688 A | * | 4/1978 | F16K 11/22 |
| GB | 1591467 A | * | 6/1981 | G01N 1/14 |
| JP | 56114762 A | * | 9/1981 | 422/63 |
| JP | 59092328 A | * | 5/1984 | G01N 1/14 |
| JP | 02145969 A | * | 6/1990 | 422/64 |
| JP | 07229885 A | * | 8/1995 | G01N 30/24 |
| WO | 90/09431 | | 8/1990 | |
| WO | WO 2007004763 A1 | * | 1/2007 | G01T 1/16 |
| WO | 2007125023 | | 11/2007 | |
| WO | 2007125023 A1 | | 11/2007 | |

OTHER PUBLICATIONS

Japanese Office Action (English translation) dated Jul. 30, 2013 for Japanese application No. 2011-265576.

* cited by examiner

AUTOMATED ASEPTIC SAMPLING WORKSTATION AND SAMPLE COLLECTION DEVICES THEREFORE

BACKGROUND OF THE INVENTION

1. Field of the Invention

The present disclosure relates to automated aseptic sampling workstations. More particularly, the present disclosure relates to workstations for use in the automated taking of product samples during the processing of various fluids, as well as to sample collection devices used with such automated workstations.

2. Description of Related Art

The processing of many fluid products can be performed in a sterile environment and/or an aseptic environment to protect the product and/or the manufacturing personnel from contamination. Such fluid products can include, but are not limited to, pharmaceutical products (e.g., medicines and vaccines), food products, biological products, biochemical products, chemical products, and any combinations thereof. During such processing, it is known to sample or test the fluid product before, during, and after certain processing steps to ensure that the resultant product meets various acceptance criteria.

In some instances, the sampling can be performed during or after certain process steps and/or at certain time intervals. In other instances, the sampling can be performed after the product has been made, but before the production batch is released for use by consumers.

Importantly, the taking of a sample from the processing line is a critical activity and creates a potential risk of contaminating the product and/or the sample. Unfortunately, the risk of contamination often leads manufacturers to limit the number of samples that are obtained and/or to limit the number of locations where such samples are obtained.

In addition, contamination of the sample may cause a false result, which can lead to the unneeded destruction of a product batch and/or unneeded delay in the continuation of the production process until the cause of the contamination is determined. Further, the need to clean and sterilize the sample path before and/or after each batch typically requires the sampling devices to be hard piped into a specific location in the production line, which can limit the flexibility of the processing line to process other products in a timely and efficient manner.

Further, the samples that are taken must be properly identified by the operator responsible for taking the sample and this identifying information must then subsequently be input by the department responsible department responsible for testing the sample. The manual identification of samples by the sample taker and the manual input of this identity by the sample tester have proven to be error prone, which can further complicate the proper testing and release of product.

Accordingly, it has been determined by the present disclosure that there is a need for workstations that can overcome, alleviate, and/or mitigate one or more of the aforementioned and/or other deleterious effects of the prior art. For example, it has been determined by the present disclosure that there is a need for workstations that automate sampling of fluid products, while ensuring sample integrity and eliminating the risk of sample and product contamination, and minimizing errors related to manual input of data related to the samples.

BRIEF SUMMARY OF THE INVENTION

A sample collection device is provided. The collection device includes an input conduit, a plurality of automated sample collection bags, a waste collection bag, and a valve block. The input conduit is connectable to a fluid processing line. The automated sample collection bags each have a sample volume and the waste collection bag has a waste volume. The valve block a plurality of three-way valves and an output, where the plurality of three-way valves correspond in number to the plurality of automated sample collection bags, each of the three-way valves placing the input conduit in fluid communication with a different one of the plurality of sample collection bags. The output is in fluid communication with said waste collection bag. The collection device has a ratio of the waste volume to the sample volume of not more than 15:1.

An automated sample collection workstation is provided. The workstation includes a processor, a peristaltic pump, a valve actuator, and an algorithm. The peristaltic pump and the valve actuator are in electrical communication with the processor. The valve actuator can move a plurality of valves, when disposed therein, among an off position, a flush position, and a sample position. The algorithm is resident on the processor and is configured to: move all of the valves to the off position and place the pump in an off state when no sampling or flushing is required, move all of the valves to the flush position and place the pump in an on state for a predetermined flush time period when flushing is required, and move a respective one of the valves to the sample position, move any of the valves upstream of the respective valve to the flush position, and place the pump to the on state for a predetermined sample time period when a sample is required.

A method of automatically taking a plurality of fluid samples from a processing line is provided. The method includes: cleaning a processing line having a first half of a two-part connector connected thereto; connecting a second half of the two-part connector to the first part, the second half part of a sample collection device, the sample connection device having a plurality of collection bags, a valve block, and an input conduit with the second half of the two-part connector, the valve block having an input, a plurality of three-way valves, and an output, the plurality of three-way valves corresponding in number to the plurality of collection bags, each of the three-way valves placing the input in fluid communication with a different one of the plurality of collection bags, the output being in fluid communication with a waste collection bag, the input being in fluid communication with the input conduit; and inserting the valve block into a valve actuator so that a handle of each of the plurality of valves is movable by the valve actuator.

A method of automatically taking a plurality of fluid samples from a processing line is also provided that includes: placing an input conduit of a sample collection device in fluid communication with the processing line; operatively coupling the input conduit to a peristaltic pump and to an input of a valve block having a plurality of three-way valves; operatively coupling the valve block to a valve actuator so that each of the plurality of three-way valves is movable by a different portion of the valve actuator among an off position, a flush position, and a sample position; controlling the valve actuator to move all of the plurality of three-way valves to the flush position and turning on the peristaltic pump so that fluid from the processing line is pumped through the valve block to a waste bag in fluid communication with an output of the valve block; and controlling the valve actuator to move a particular valve of the plurality of three-way valves to the sample position and to move any of the plurality of three-way valves upstream of the particular valve to the flush position while the peristaltic pump remains on, the particular valve being associated with a particular sample bag so that fluid from the processing line is pumped through the valve block to the particular sample bag.

The above-described and other features and advantages of the present disclosure will be appreciated and understood by those skilled in the art from the following detailed description and drawing.

DETAILED DESCRIPTION OF THE INVENTION

Referring to the figures, and in particular to FIGS. 1 through 4, an exemplary embodiment of an automated aseptic sampling workstation according to the present disclosure is shown and is generally referred to using reference numeral 10. Workstation 10 is configured to automatically aseptically sample, label, and store, in sample collection device 12 (shown in FIG. 5), a plurality series of fluid samples from a processing line or vessel (A).

Figure 1:
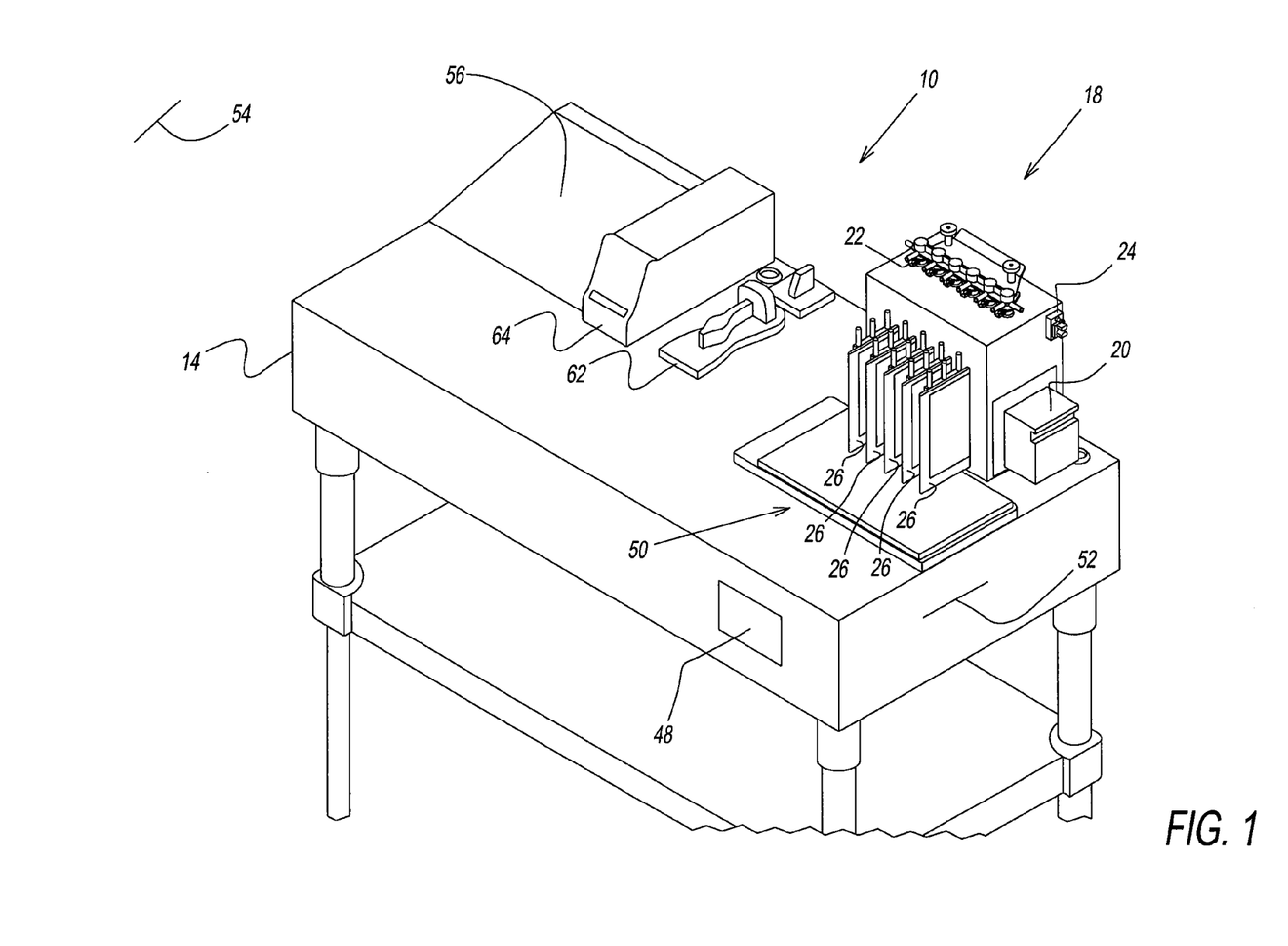
FIG. 1 is a front, top perspective view of an exemplary embodiment of a workstation according to the present disclosure.

Workstation 10 is configured to automatically sample fluid samples including samples such as, but not limited to, pharmaceutical products (e.g., medicines and vaccines), food products, biological products, biochemical products, chemical products and any combinations thereof.

Advantageously, workstation 10 is flexibly configured, namely is configured so that the workstation can be moved from point-to-point and/or from one process step to another process step in a manufacturing process. Further, workstation 10 is preferably suitable for use in an aseptic or clean room environment such that the material selection (e.g., stainless steel or other material) and material specifications (e.g., surface finish) are sufficient for use in such environments.

Figure 2:
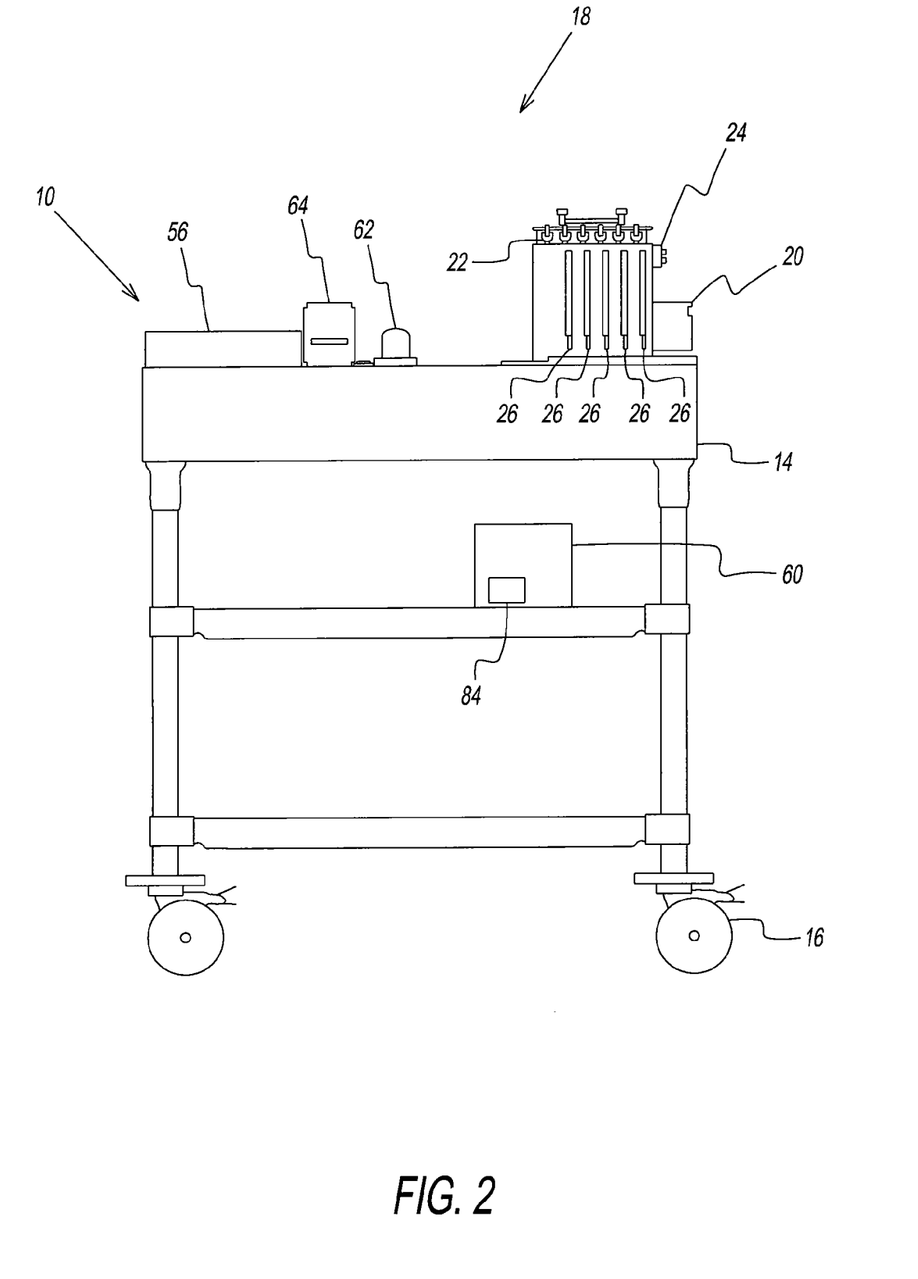
FIG. 2 is a front plan view of the workstation of FIG. 1.
Figure 3:
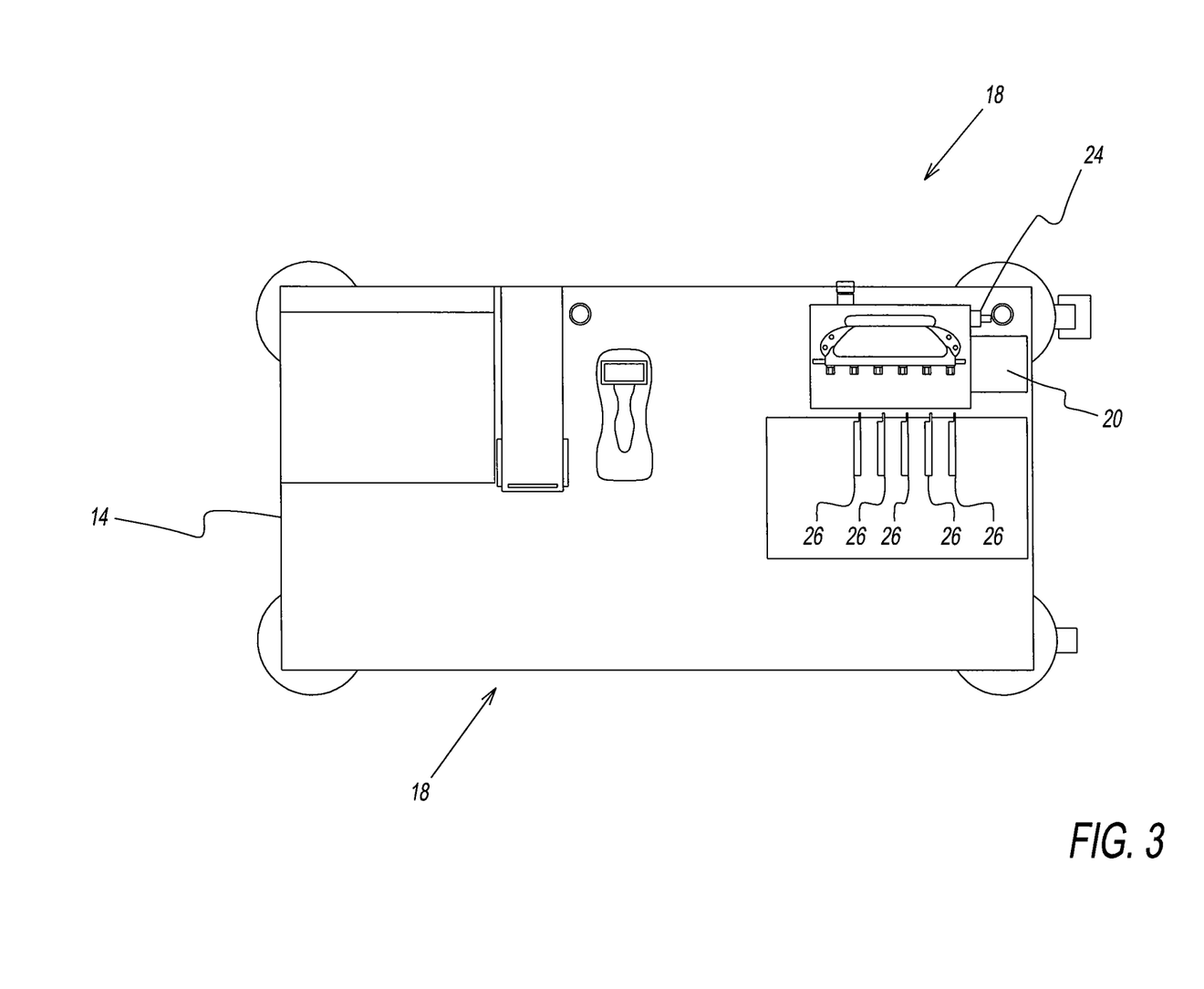
FIG. 3 is a top view of the workstation of FIG. 1.

Workstation 10 includes a base or cabinet 14 supported, in some embodiments, by a plurality of wheels or casters 16 such that the workstation is mobile and can be positioned, as desired, in various locations within a processing facility.

Figure 4:
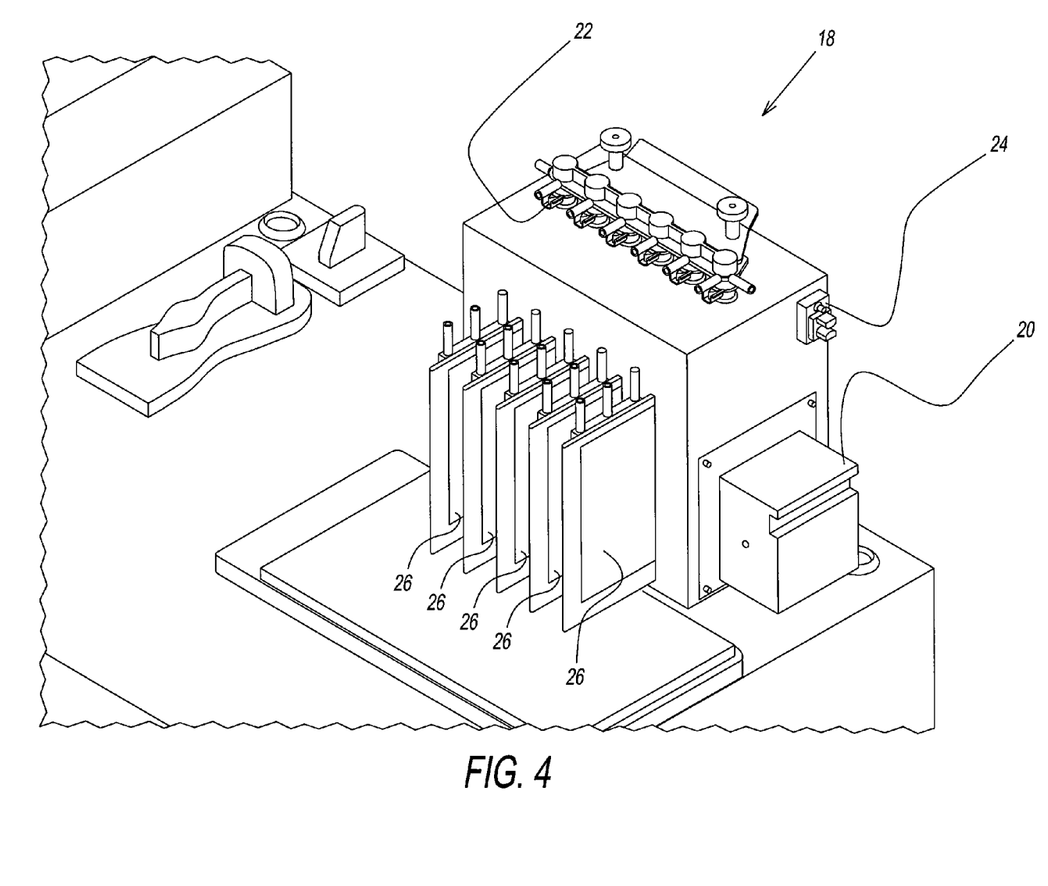
FIG. 4 is a front, top perspective view of an exemplary embodiment of a sampling portion of the workstation of FIG. 1.

Workstation 10 is includes sampling portion 18 for pumping a fluid sample into sample collection device 12. Sampling portion 18 includes a pump 20, a valve actuator 22, in some embodiments, a liquid edge detector 24, and a plurality of sample holding areas 26.

Pump 20 can be any desired pumping device but is, preferably, a non-contact pump that selectively draws fluid samples without directly contacting the fluid itself. In a preferred embodiment, pump 20 is a peristaltic pump.

Liquid edge detector 24 can be any desired detector such as, but not limited to a sonic, a capacitance, or any other non-contacting or contacting sensor for determining the presence and absence of liquid in one or more areas of sample collection device 12. Detector 24 can be in electrical communication with workstation 10 so that the workstation can detect when fluid is present in a predetermined location in sample collection device 12.

Figure 5:
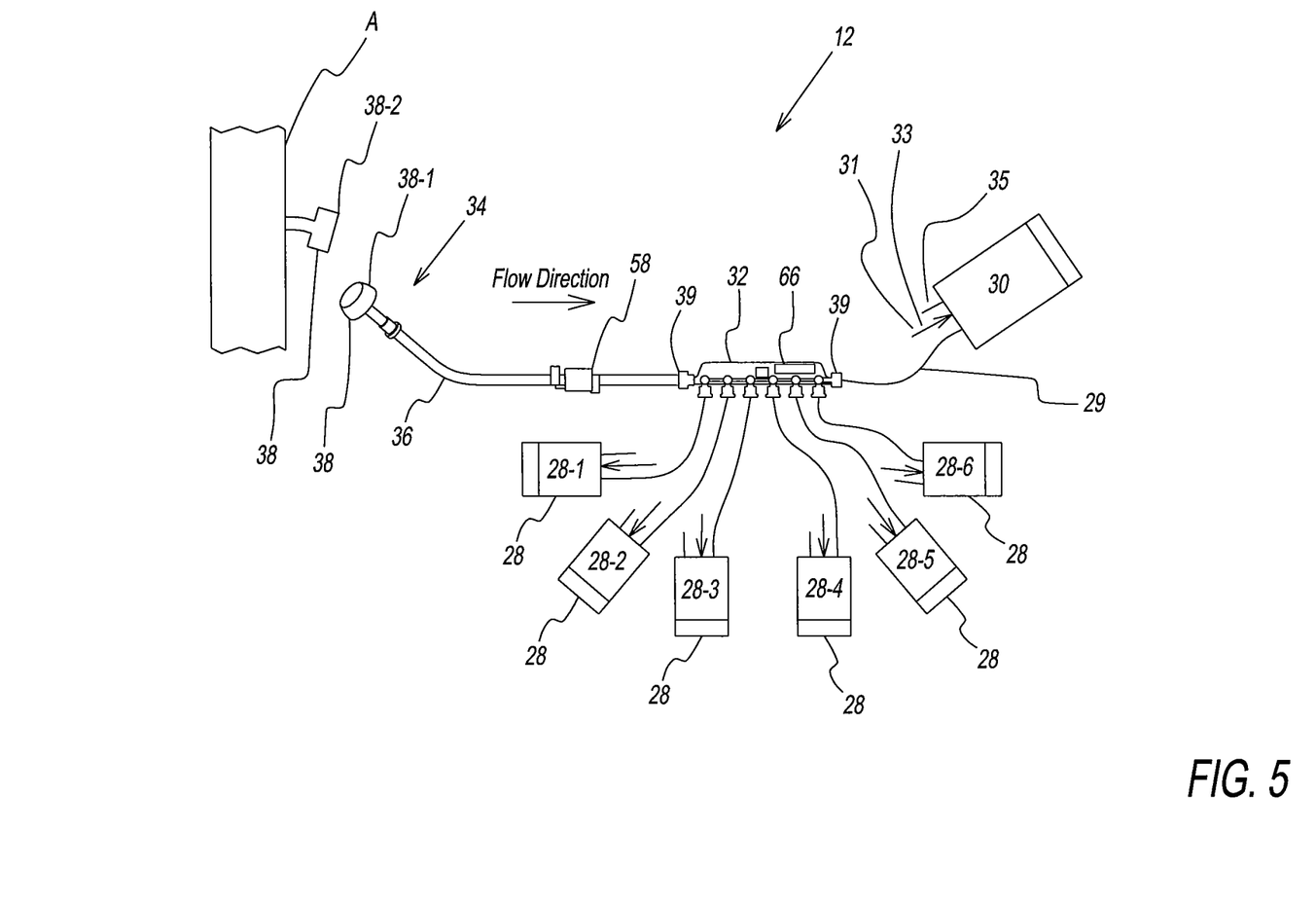
FIG. 5 is a perspective view of an exemplary embodiment of a sample set according to the present disclosure for use with the workstation of FIG. 1.

As seen in FIG. 5, sample collection device 12 includes a plurality of sample collection bags 28 (six shown), at least one waste bag 30 (only one shown), and a valve block 32. Sample bags 28 can be configured to have any desired volume so that the volumes of the sample bags are identical to one another and/or different from one another.

Sample bags 28 and waste bags 30 can be any desired collection receptacle such as, but not limited to the Allegro™ 2D Biocontainer, which is commercially available from Pall Corporation. In this embodiment, each bag 28, includes an input line 29 releasably sealed with a clamp 33, an output line 31 releasably sealed with a clamp 33, and a port 35.

In the illustrated embodiment, sample collection device 12 include five automated sample bags 28 of identical volume, e.g., about 50 milliliters (mL), and one manual sample bag 28 of a larger volume, about 500 ml. Also, in the illustrated embodiment, the sample collection device 12 includes one waste sample bag 30 of about 1,000 mL. Of course, it should be recognized that the number and volumes of bags 28, 30 can be modified to any desired size.

Device 12 further includes an input conduit 34 configured to place the processing line in fluid communication with valve block 32.

Input conduit 34 includes at least one flexible portion 36. Portion 36 is configured to operably mate with pump 20 so that the pump can force the fluid sample into bags 28, 30 of sample collection device 12. In the example where pump 20 is a peristaltic pump, flexible portion 36 is made of a material having sufficient resiliency (e.g., silicone tubing) to operate in cooperation with the peristaltic pump.

Sample collection device 12 find use with one or more two-part, aseptic connectors 38. In the illustrated embodiment, input conduit 34 has only one part 38-1 of a two-part connector 38 connected thereto. The mating part 38-2 for two-part connector 38 of input conduit 36 is in fluid communication with processing line or vessel A.

In this manner, sample collection device 12 can be fluidly connected to the processing line or vessel by joining both halves 38-1, 38-2 of two part-connector 38 at the input conduit and the processing line or vessel to one another. In order to maintain sterility, the portion of the two-part connector 38-2 mated with the production line or vessel A can be sterilized or sanitized along with the production line or vessel before processing of the fluid.

Two-part connector 38 can be any disposable, two-part aseptic connector such as, but not limited to the Kleenpak™ connector, which is commercially available from Pall Corporation, the Opta® SFT-I connector, which is commercially available from Sartorius Stedim Biotech, the Lynx® ST connector, which is commercially available from Millipore Corporation, and the AseptiQuik™ connector, which is commercially available from Colder Products Corporation.

In some embodiments of sample collection device 12, sample bags 28, waste bag 30, and valve block 32 are removably connected to one another. For example, sample collection device 12 can include a plurality of connectors 39 such as, but not limited to Luer lock connectors.

All product contact surfaces within collection device 12 are made of any material sufficient to hold or contact the sample fluid without interacting or contaminating the sample. Moreover, collection device 12 can be packaged within one or more outer wrappings (not show) then can be sterilized using known sterilization methods such as, but not limited to, gamma irradiation. In this manner, collection device 12 can remain in a sterile condition until ready for use.

Figure 6:
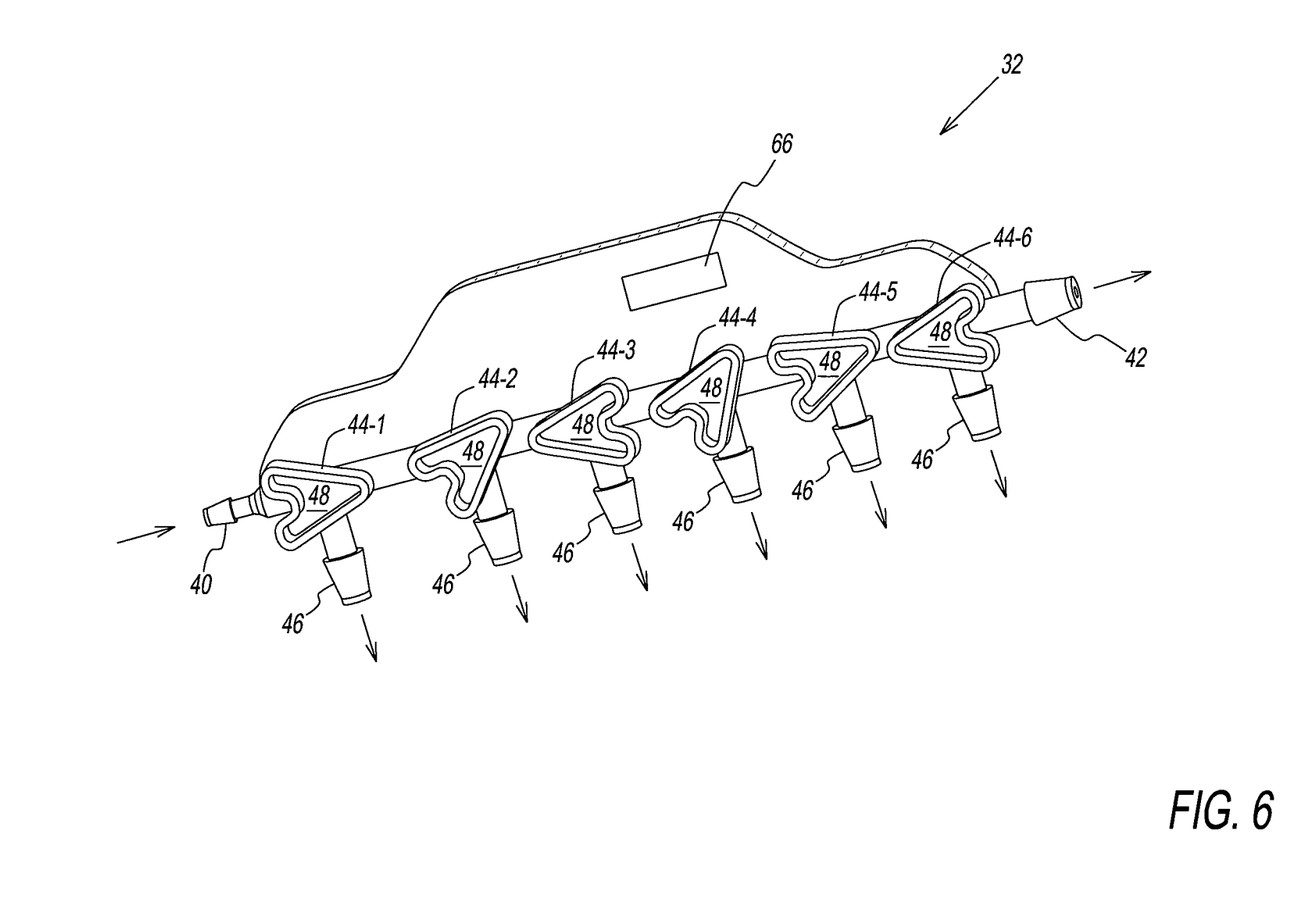
FIG. 6 is a perspective view of an exemplary embodiment of a valve block according to the present disclosure for use in the sample set of FIG. 5.

Valve block 32, as shown in FIG. 6, includes an input 40, a waste output 44, and a plurality of three-way valves 46 (six shown). The input 40 is in fluid communication with input conduit 34 and waste output 42 is in fluid communication with waste collection bag 30.

The plurality of three-way valves 44 correspond in number to the plurality of collection bags 28, with a sample output 46 from each of the valves being in fluid communication with a different collection bag 28.

Three-way valves 44 are each movable by rotation of a valve handle 48 among three positions: an "off" position; a "flush" position; and a "sample" position.

In the off position, each valve 44 prevents fluid from input 40 from flowing through the valve to either waste output 42 or sample output 46. In the flush position, each valve 44 allows fluid from input 40 to flow through the valve towards waste output 42, but prevents flow toward its respective sample output 46. In the sample position, each valve 44 allows fluid from input 40 to flow through the valve towards the respective sample output 46, but prevents flow toward the waste output 42.

Handle 48 of each valve 44 operably mates with a different portion of valve actuator 22 so that the valve actuator can selectively rotate each handle independently of one another among the three positions. In this manner, workstation 10, via valve actuator 22, is configured to actuate valve block 32 to selectively divert sampled fluid from the processing line or vessel into any one of sample bags 28 or waste bag 30.

Referring now to Table No. 1 below, the relative positions of valves 44 are provided during various sampling activities contemplated by the present disclosure.

Here, the plurality of valves 44 are sequentially numbered, in the direction of fluid flow, as valves 44-1 through 44-6 and the sample bags 28 are sequentially numbered, in the direction of fluid flow, as bags 28-1 through 28-6.

TABLE NO. 1

| | VALVE POSITION | | | | | |
| --- | --- | --- | --- | --- | --- | --- |
| | Valve 44-1 | Valve 44-2 | Valve 44-3 | Valve 44-4 | Valve 44-5 | Valve 44-6 |
| Not in use | Off | Off | Off | Off | Off | Off |
| Flush to waste bag 30 | Flush | Flush | Flush | Flush | Flush | Flush |
| Sample to bag 28-1 | Sample | Off | Off | Off | Off | Off |
| Sample to bag 28-2 | Flush | Sample | Off | Off | Off | Off |
| Sample to bag 28-3 | Flush | Flush | Sample | Off | Off | Off |
| Sample to bag 28-4 | Flush | Flush | Flush | Sample | Off | Off |
| Sample to bag 28-5 | Flush | Flush | Flush | Flush | Sample | Off |
| Sample to bag 28-6 | Flush | Flush | Flush | Flush | Flush | Sample |

As seen in Table No. 1 above, when sample collection device 12 is not in use, all of the valves 44 are rotated to the "off" position, preventing fluid communication through valve block 32.

Before sampling and/or whenever it is desired to flush or prime the fluid flow path within sample collection device 12, each of the valves 44 can be rotated to the "flush" position, placing input 40 in fluid communication with output 42. In this manner, fluid from input conduit 34 is diverted to waste bag 30.

When sampling to a particular sample bag 28 is desired, the particular valve 44 associated with that particular bag 28 is moved to the "sample" position. Further, any valve upstream, with respect to fluid flow through valve block 32, is moved to the flush position. Preferably, any valve 44 downstream, with respect to fluid flow through valve block 32, is moved to the off position. However, these downstream valves 44 can have any desired state.

When the sampling to a particular sample bag 28 is completed, valves 44 are returned to the "off" position.

In use, sample collection device 12 is positioned in workstation 10 so that flexible portion 36 of input conduit 34 is operatively positioned in pump 20 and so that valve block 32 is operatively positioned in valve actuator 22. When fluid is being process through the production line or vessel, the half of two-part connector 38 at input conduit 34 is operatively connected to its mating half arranged on the line or vessel.

Valve actuator 22 can be used by the operator to manually operate valves 44. For manual operation, workstation 10 includes one or more valve operating buttons or controls 48.

Alternately, and in a preferred embodiment, valve actuator 22 can be automatically controlled by workstation 12 as described in more detail herein below. Of course, it is contemplated by the present disclosure for valve actuator 22 to be controlled by any combination of manual and automated control.

It has been determined by the present disclosure that workstation 10, due to in part the use of two-part, aseptic connectors 38 in combination with sample collection device 12, can be selectively moved from point-to-point within the manufacturing process to perform the desired sampling as needed. Also, workstation 10 can be installed in a particular location within the manufacturing line when that line is set up to make a first product, but can then be relocated to a different location within the manufacturing line when that line is set up to make a second product. In other words, workstation 10 can reduce the equipment cost to monitor a manufacturing process by being used in multiple locations within the manufacturing line during a production run or by being repositioned to a different stationary position when the manufacturing line is reconfigured to accommodate the manufacture of different products.

Workstation 10 can, in some embodiments, include a sample and waste bag holding area 50, which can maintain bags 28, 30 in a desired position and/or in a desired conditions suitable for the samples contained therein. For example, workstation 10 can include environmental controls sufficient to maintain bags 28, 30, and thus, samples contained therein, at a desired temperature. In other examples, workstation 10 can include agitation and/or vibration devices sufficient to maintain the sample within bags 28, 30 in a mixed or agitated state.

Workstation 10 can include one or more sensors 52 to monitor and record the conditions (e.g., temperature, humidity) within base 14, the conditions within bags 28, 30 (e.g., temperature, turbidity, volume, etc), and other conditions of the workstation. Additionally, workstation 10 can include sensors or can connect to sensors outside 54 the workstation to monitor and records the conditions outside the base 12 including but not limited to temperature, pressure, humidity, particulates, and detection, typing and monitoring of viral and/or microbial organisms.

It is contemplated by the present disclosure for workstation 10 to coordinate the control of pump 20, valve actuator 22, liquid edge detector 24 and sensors 50 within workstation 10 as well as collection of signals and data from any other (wireless or hardwire connected) human-machine input devices 56 such as, but not limited to, keyboards, and touch screens or any other data communication devices, USB or other data communication ports, CD or other data reading devices, computers, PLC's, analyzing equipments, testing devices and sensors outside the workstation.

In some embodiments, sample collection device 12 can include a disposable flow meter 58 in electrical communication with workstation 10.

Thus, workstation 10 can include a processor 60 having human-machine-interface (HMI) 56 with one or more input devices 62 and one or more output devices 64. Processor 60 can include devices such as, but not limited to, a computer, a programmable logic controller (PLC), or any other processor suitable to control the various components of workstation 10.

HMI 56 can includes, for example, a keyboard, a mouse, a bar-code reader, a touch screen, a USB or other data communication port, CD or other data reading device, a remote control, or any other data communication device suitable for inputting commands to processor 60 in a wired and/or a wireless manner, and any combinations thereof.

Output device 64 can include a computer monitor, an audible alarm device, a visual alarm device, a printer, a USB or other data communication port, a CD or other data writing device, a (wireless or hard-wired) data communication device or any other device suitable for receipt of a wired and/or a wireless output from processor 60.

In a preferred embodiment, HMI 56 includes at least one bar code reader 62 and sample collection device 12 can include at least one machine readable label 66, which includes details regarding the sample collection device such as, but not limited to, the lot number, the expiration date, the number of sample and waste bags 28, 30, the volume of sample and waste bags 28, 30, the volume of conduits within the collection device, and other details. In use, the operator can scan machine readable label 66 of sample collection device 12 using bar code reader 62 so that processor 60 can determine and record the various details regarding the sample collection device 12.

Further, it is contemplated by the present disclosure for output devices 64 to include at least one printer. Processor 60 controls printer 64 to print labels, which can be applied by the operator directly on each bag 28, 30 and includes information that is relevant to the sample contained within the bag. For example, processor 60 can control printer 64 to print information such as, but not limited to, date of sample, time of sample, operator, batch ID, program sequence, room number, station number, sample location, and other process or environmental variables.

Preferably, printer 64 is configured to print information on the label in a machine readable language, such as a bar code, so that a laboratory technician can scan the machine readable code to input all relevant data related to the sample within the bag, which can mitigate instances of data entry errors.

Processor 60 is in electrical communication via any wireless or wired manner such as, but not limited to, electrical, optical, audible, infrared, radiofrequency, magnetic and other means of communication with any one or more of pump 20, valve actuator 22, level sensor 24, manual controls 48, sensors 52 and 54, HMI 56, flow meter 58, output devices 60, as well as bar code reader 62 and printer 64.

In this manner, processor 60 is configured to coordinate the control of workstation 10 and the collection of samples in collection device 12, as well as to provide information on labels for placement onto bags 28, 30.

In some examples, processor 60 can communicate in wired and/or wireless manner with one or more computers (not shown) external to workstation 10, where such external computers can include data collection, data archiving, data analysis and data management software.

The aseptic sampling ability of workstation 10 and sample collection device 12 mitigate or eliminate the risk of contaminating the sample obtained or the processing line.

Workstation 10, via processor 60, can be programmed to aseptically obtain one or a series of samples taken randomly, at manual selected times or at pre-set times and with manually selected volumes or pre-set volumes.

Figure 7:
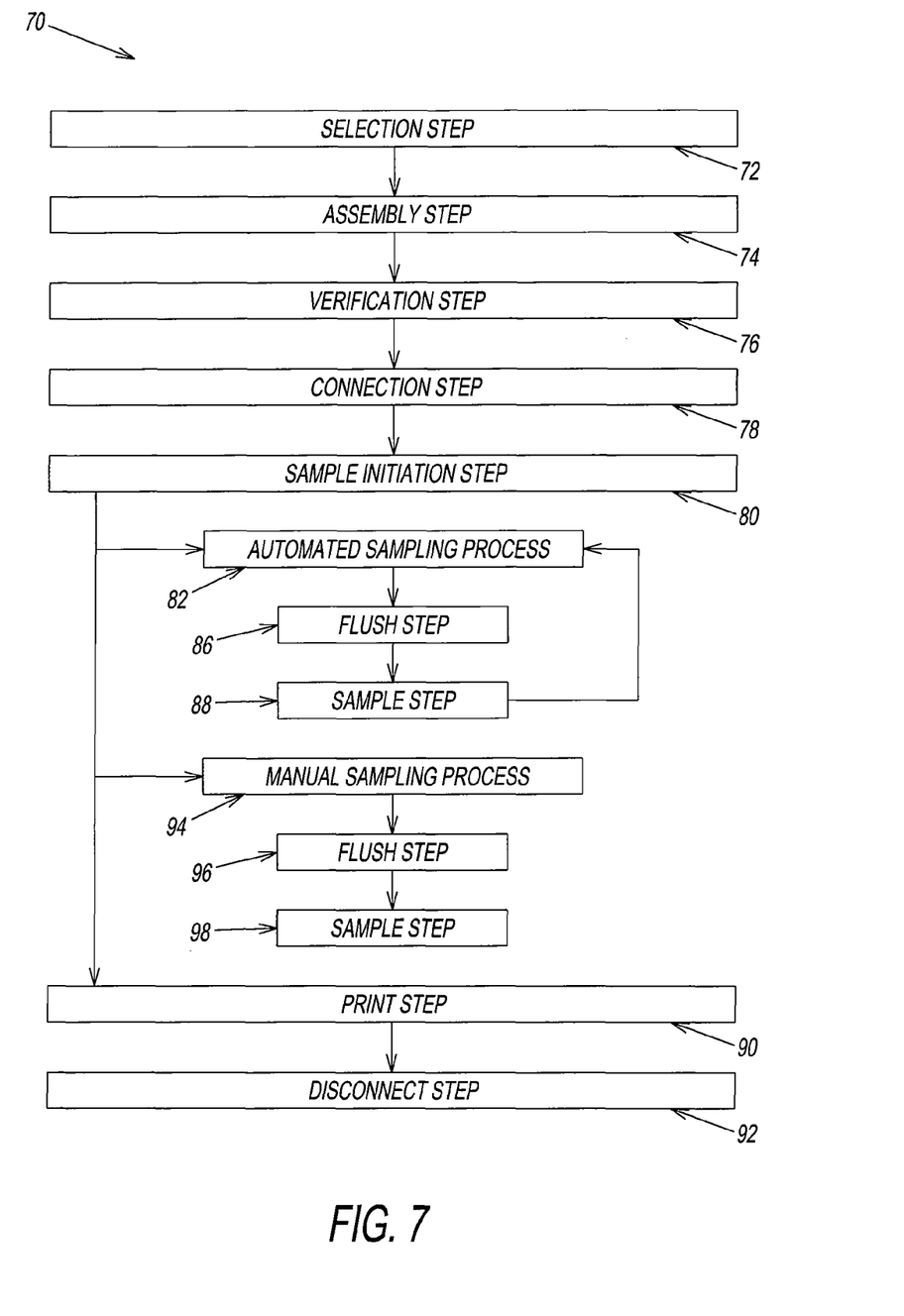
FIG. 7 is a flowchart illustrating an exemplary embodiment of a sampling method according to the present disclosure.

Referring now to FIG. 7, a method 70 of operating workstation 10 having sample collection device 12 is shown.

In a first or selection step 72, the appropriate sample collection device 12 for desired sampling is selected by the operator.

In a second or assembly step 74, the operator assembles the selected sample collection device 12 in workstation 10. Specifically, bags 28, 30 are placed in area 50, valve block 32 is operatively positioned in valve actuator 22, and flexible portion 36 of input conduit 34 is operatively positioned in pump 20. When level liquid edge detector 24 is present, a portion of input conduit 34 is operatively positioned in the detector.

In a third or verification step 76, the operator inputs information related to the sample collection device 12 into processor 60 and inputs information related to the desired processing line or vessel from which workstation 10 will be taking samples. In some embodiments, the verification step 76 includes requiring the operator to use scanner 62 to scan bar code 66 on sample collection device 12.

Once processor 60 verifies sample collection device 12, the processor sends an output to the operator in a fourth or connection step 78 to instruct the operator to place the sample collection device in fluid communication with the processing line or vessel via HMI 56. As discussed in detail above, sample collection device 12 is placed in fluid communication with the processing line or vessel by interconnecting two-part connector 38.

When the fluid is present in the processing line or vessel, the operator initiates a desired sampling sequence of workstation 10 during step 80. Step 80 may initiate a manual sampling process 82 using manual controls 48. Alternately, step 80 may initiate an automated sampling process using an algorithm 84 resident on processor 60.

During automated sampling process, algorithm 84 is configured to activate pump 20 to force fluid from the processing line or vessel through input conduit 34 and valve block 32 and into, as desired, any one of sample bags 28 and waste bag 30.

Before taking each sample, algorithm 84 is configured to control workstation 10 to a flush step 86. During flush step 86, algorithm 84 flushes or purges fluid through sample collection device 12 into waste bag 30 for a predetermined period of time by moving all of the valves 44 to the "flush" position.

Then, after the predetermined purge or flush of step 86, algorithm 84 initiates a sample step 88 in which the processor 60 moves the plurality of valves 44 in the manner discussed above with respect to Table No. 1 to divert a sample into the desired collection bag 28.

After a predetermined volume of sample fluid has been diverted into the selected collection bag 28, algorithm 84 completes the sample step 88 by deactivating pump 20 and returning the valves 44 to the "off" position.

Algorithm 84 repeats the flush and sample steps 86, 88 to activating pump 20 to flush fluid within sample collection device 12 to waste bag 30, divert the sample to the desired sample bag 28, deactivates the pump, and closes the valves until all of the desired samples have been obtained.

In embodiments where sample collection device 12 includes flow meter 58, algorithm 84 can use inputs from the flow meter to ensure proper sample and purge volumes. Similarly, in embodiments where workstation 10 includes fluid edge sensor 24, algorithm 84 can use inputs from the sensor to ensure proper sample and purge volumes.

Preferably, algorithm 84 is further configured to activate printer 64 to print data onto a label when a respective sample is obtained during a print step 90. The operator can then apply the label on the appropriate sample bag 28, respectively. Similarly, algorithm 84 can be configured to activate printer 64 to print waste related data onto a label when the respective waste is collected or after all of the waste has been collected.

During manual sampling process 94, the operator can manually and/or via controller 60 flush sample collection device 12 to waste bag 30 during a manual flush step 96 and divert a sample to the manual sample bag 28, when present, during a manual sample step 98.

Once all of the samples have been obtained, the operator can, during a disconnection step 92, disconnect sample collection device 12 from the processing line or vessel by separating two-part connector 38. Similarly, the operator can remove each sample bag 28 and waste bag 30 from sample collection device 12 by separating two-part connectors 38.

Advantageously, algorithm 84 purges a predetermined amount fluid from with sample collection device 12 before taking each sample to ensure that the fluid collected in sample bag 28 is representative of fluid in the processing line or vessel at the time of the sample.

In order to perform the desired purging, waste bag 30 has a volume that is sufficient to hold the purged fluid. In the illustrated embodiment, a ratio of the volume of the waste bag 30 to the volume of the sample bag 28 is not more than 15:1, more preferably 10:1, with between 5:1 to 2:1 being most preferred. In this manner, waste bag 30 provides a volume sufficient to allow sample collection device 12 to be flushed before taking each of the samples to ensure that the fluid collected in the sample bag 28 is representative of the liquid in the processing line and, not, fluid remaining within the sample collection from the prior sample.

Figure 8:
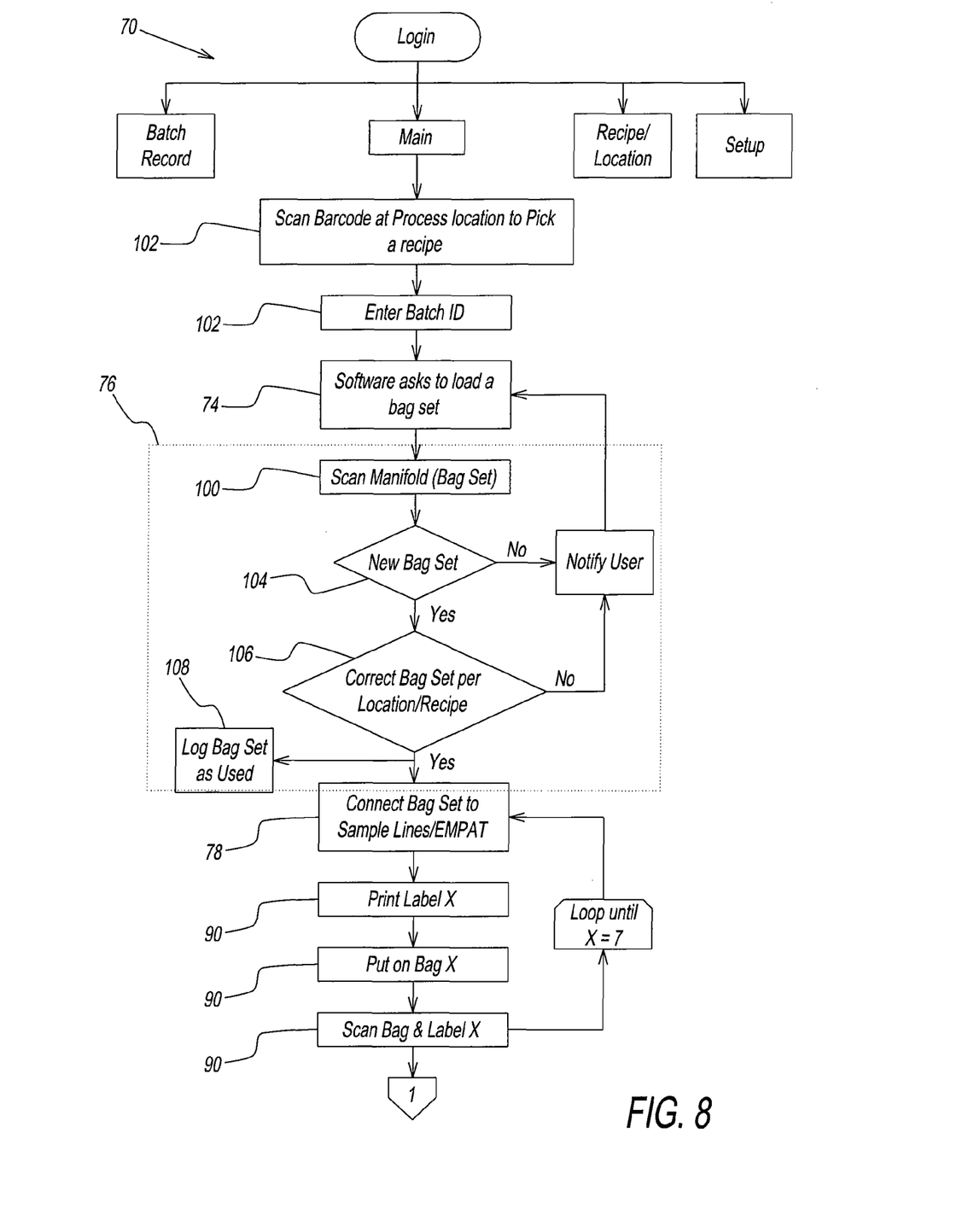
FIG. 8 is a flowchart illustrating an exemplary embodiment of a sample collection device verification method according to the present disclosure.

Referring now to FIG. 8, an exemplary embodiment of verification step 76 from method 70 is shown in more detail. During verification step 76, processor 60 requires the user to scan bar code 66 on sample collection device 12 using scanner 62 in a scanning step 100.

In some embodiments, prior to scanning step 94, method 70 can further include a process identification step 102, where parameters and/or details of the process and/or liquid to be sampled are entered into processor 60. The parameters and/or details can be entered manually into processor 60 by the operator, can be scanned into processor 60 using scanner 62 and an identifier located on the batch record and/or the process equipment, or any combination of manual and scanning data entry.

Verification step 76 determines, based on data within processor 60 and information from bar code 66, whether sample collection device 12 is new or has been previously used at a step 104. If the sample collection device 12 has been previously used, verification step 76 returns the user to assembly step 74 so that a new collection device can be used.

If the sample collection device 12 is new, verification step 76 compares the details of the sample collection device (e.g., size and number of bags 28, 30) to the sample protocol stored within processor 60 for the process being monitored at step 106. If the sample collection device 12 is not correct for the samples that are required, verification step 76 returns the user to assembly step 74 so that a correct collection device can be used.

If the sample collection device 12 is correct, verification step 76 logs sample collection device 12 as being previously used within processor 60 at step 108 and instructs the operator at connection step 78 to place the sample collection device in fluid communication with the processing line or vessel via HMI 56. As discussed in detail above, sample collection device 12 is placed in fluid communication with the processing line or vessel by interconnecting two-part connector 38.

It should also be noted that the terms "first", "second", "third", "upper", "lower", and the like may be used herein to modify various elements. These modifiers do not imply a spatial, sequential, or hierarchical order to the modified elements unless specifically stated.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the present disclosure.

What is claimed is:

1. An automated sample collection workstation, comprising:
   a processor;
   a pump in communication with said processor;
   a valve actuator in communication with said processor, said valve actuator configured to move a plurality of valves, when disposed therein, among an off position, a flush position, and a sample position; and
   an algorithm resident on said processor, said algorithm configured to:
      move all of said plurality of valves to the off position and place said pump in an off state when no sampling or flushing is required,
      move all of said plurality of valves to the flush position and place said pump in an on state for a predetermined flush time period when flushing is required, and
      move a respective one of said plurality of valves to said sample position, move any of said plurality of valves upstream of said respective one to said flush position, and place said pump to said on state for a predetermined sample time period when a sample is required.

2. The sample collection workstation of claim 1, further comprising a bar code scanner in communication with said processor.

3. The sample collection workstation of claim 1, further comprising a label printer in communication with said processor.

4. The sample collection workstation of claim 1, further comprising a fluid edge detector in communication with said processor.

5. The sample collection workstation of claim 1, further comprising a sensor in communication with said processor, said sensor being configured to detect an environmental condition.

6. The sample collection workstation of claim 1, further comprising a base supported by a plurality of wheels, wherein said processor, said pump, and said valve actuator are disposed on said base.

7. The sample collection workstation of claim 6, wherein said base further comprises a sample and waste bag holding area, which can maintain sample and waste bags in a desired position and/or in desired conditions suitable for the samples contained therein.

8. An automated sample collection system, comprising:
- a processor;
- a valve actuator controlled by said processor to move a plurality of valves, when disposed therein, among a first position, a second position, and a third position; and
- an algorithm resident on said processor, said algorithm configured to:
  - move all of said plurality of valves to the second position for a predetermined flush time period when flushing is required, and
  - move a respective one of said plurality of valves to said third position, move any of said plurality of valves upstream of said respective one to said second position.

9. The sample collection system of claim 8, further comprising a pump in communication with said processor.

10. The sample collection system of claim 9, wherein said algorithm is configured to move all of said plurality of valves to the first position and place said pump in an off state when no sampling or flushing is required.

11. The sample collection system of claim 9, wherein said algorithm is further configured, when the flushing is required, to place said pump in an on state for a predetermined flush time period.

12. The sample collection system of claim 9, wherein said algorithm is further configured, when the sample is required, place said pump to said on state for a predetermined sample time period.

13. The sample collection system of claim 8, further comprising a bar code scanner in communication with said processor, wherein one or more parameters of said algorithm are selected based on information collected by said bar code scanner.

14. The sample collection workstation of claim 8, further comprising a label printer in communication with said processor.

15. The sample collection system of claim 8, further comprising a fluid edge detector in communication with said processor.

16. The sample collection system of claim 8, further comprising a sensor in communication with said processor, said sensor being configured to detect an environmental condition.

* * * * *